US006536264B1

United States Patent
Flammersfeld et al.

(10) Patent No.: US 6,536,264 B1
(45) Date of Patent: Mar. 25, 2003

(54) APPARATUS FOR DETECTING COOLANT CORROSIVENESS

(75) Inventors: Stephen K. Flammersfeld, Ann Arbor, MI (US); Ian Daniel McKenzie, Canton, MI (US); David Lloyd Hart, Ann Arbor, MI (US)

(73) Assignee: Detroit Diesel Corporation, Detroit, MI (US)

( * ) Notice: Subject to any disclaimer, the term of this patent is extended or adjusted under 35 U.S.C. 154(b) by 0 days.

(21) Appl. No.: 10/045,758

(22) Filed: Apr. 11, 2002

(51) Int. Cl.[7] ............................................. G01N 17/00
(52) U.S. Cl. ...................................................... 73/86
(58) Field of Search ........................... 73/86; 324/71.2; 200/61.04, 61.08

(56) References Cited

U.S. PATENT DOCUMENTS

| 3,621,810 A | * | 11/1971 | Zuck, Jr. .................... 116/283 |
| 3,787,650 A | * | 1/1974 | Lewis ....................... 200/61.04 |
| 4,313,042 A | * | 1/1982 | Ehrhart .................... 200/61.04 |
| 4,333,516 A | * | 6/1982 | Krueger et al. ............ 165/134.1 |
| 4,338,997 A | * | 7/1982 | Krueger et al. ............ 165/134.1 |
| 4,468,613 A | * | 8/1984 | Slough et al. .............. 324/71.2 |
| 5,208,162 A | * | 5/1993 | Osborne et al. .............. 436/6 |
| 5,253,674 A | * | 10/1993 | Argyle et al. ............... 137/559 |
| 5,659,128 A | * | 8/1997 | Goldenberg ............... 73/53.01 |
| 5,740,861 A | * | 4/1998 | Williams ..................... 166/66 |
| 6,131,443 A | * | 10/2000 | Duncan ......................... 73/86 |

* cited by examiner

Primary Examiner—Helen Kwok
Assistant Examiner—Charles Garber
(74) Attorney, Agent, or Firm—Brooks & Kushman P.C.

(57) ABSTRACT

An apparatus to visually check coolant corrosiveness having first and second opposing ends in spaced apart relation to each other, and a sidewall extending substantially unbroken therebetween to define a hollow body; a non corrodible coolant barrier at said first end occluding said first end and forming a water tight seal over said first end; said non corrodible barrier having a transparency in at least a portion of said barrier; a corrodible coolant barrier at said second end occluding said second end and forming a water tight seal over said second end; whereby changes in coolant pH render the coolant corrosive, which corrodes the coolant corrodible barrier, thereby allowing coolant into said hollow body to be seen through said transparency in said first end.

3 Claims, 3 Drawing Sheets

APPARATUS FOR DETECTING COOLANT CORROSIVENESS

BACKGROUND OF THE INVENTION

1. Field of the Invention

The present invention is directed to an apparatus to visually detect coolant corrosiveness.

The present invention is further directed to an apparatus for use with an internal combustion engine having a coolant systems and a coolant flow path, for visually detecting coolant corrosiveness before corrosion damage is incurred to the coolant system or engine components.

The present invention is further directed to an apparatus to be threadably inserted into the coolant flow path of an internal combustion engine to permit visual detection of coolant corrosiveness before corrosion damage is incurred to the coolant system or engine components.

The present invention further relates to an apparatus that includes a sensor in a compartment, separated from the coolant flow by a corrodible membrane. When the membrane corrodes, the sensor is immersed into the coolant, and sends a signal to an electronic unit control that sends a signal to a display on a dashboard, and may further initiate other actions and functions, thereby alerting the operator that the coolant should be checked before corrosion damage is incurred to the coolant system or engine components.

2. Description of the Related Art

Krueger et al., U.S. Pat. No. 4,333,516 discloses a corrodible container for the storage of a corrosion inhibitor to be suitably located in the coolant system of an automobile or other environment wherein the container has at least a portion thereof formed of substantially the same material and the material forming the heat exchanging device in a coolant system. The material is configured to corrode when the coolant is partially or completely replaced by a corrosive liquid such as water. The container material is thinner than the material forming the heat exchanger, and is configured to corrode before the heat exchanger corrodes, thereby releasing a coolant inhibitor to minimize the coolant corrosiveness to the heat exchanger.

Krueger '516 differs from the instant invention as set forth in the claims because there is no provision for the visual or electronic detection of coolant corrosiveness before damage is done to the engine coolant system or other engine components.

Krueger et al., U.S. Pat. No. 4,338,997 discloses a membrane for the end surface of a container for a corrosion inhibitor for engine coolant where the membrane is exposed to the coolant and corrodes when the corrosiveness of the coolant increases above a predetermined level. The membrane is formed of the same metal or alloy as the radiator and has a thin layer formed thereon of a second metal except for certain areas where the base metal is exposed so that in a corrosive environment, a galvanic cell is set up between the two metals to enhance the rate of corrosion of the membrane.

Krueger '997 differs from the instant invention as set forth in the claims because there is no provision for the visual or electronic detection of coolant corrosiveness before damage is done to the engine coolant system or other engine components.

Zamrow, U.S. Pat. No. 4,347,895 discloses a membrane for the end surface of a container for a corrosion inhibitor for engine coolant where the membrane is exposed to the coolant and corrodes when the corrosiveness of the coolant increases above a predetermined level. The membrane is formed of the same metal or alloy as the radiator and has an imperforate thin layer formed thereon of a pure form of the metal that the radiator. The imperforate thin layer is exposed to the coolant, so that in a corrosive environment, the imperforate thin layer is quickly pierced and the membrane is thereby exposed to the coolant to be corroded and release a coolant corrosion inhibitor.

Zamrow '895 differs from the instant invention as set forth in the claims because there is no provision for the visual or electronic detection of coolant corrosiveness before damage is done to the engine coolant system or other engine components.

Cheadle et al., U.S. Pat. No. 4,782,891 discloses a filter device for engine coolant that has an inlet and an out let passage for coolant flow, a dosage of coolant corrosion inhibitor, and a corrodible membrane made of magnesium or a magnesium alloy to separate the coolant corrosion inhibitor from the coolant flow. As the coolant increases in corrosiveness, the membrane is corroded and the inhibitor is released into the coolant to reduce the corrosiveness of the coolant fluid.

Cheadle et al., '891 differs from the instant invention because there is no provision in Cheadle for the visual detection or electronic of coolant corrosiveness before damage is done to the engine coolant system or other engine components.

SUMMARY OF THE INVENTION

The present invention is an apparatus to visually detect coolant corrosiveness. The apparatus is comprised of a body having first and second opposing ends in spaced apart relationship to each other, and a sidewall extending substantially unbroken therebetween to define a hollow body. A non-corrodible coolant barrier is positioned at said first end thereby occluding the first end and forming a watertight seal over the first end. In one embodiment, this barrier has a transparency in at least a portion thereof. A corrodible coolant barrier is positioned at the second end thereby occluding the second end and forming a watertight seal over the second end. Changes in coolant pH render the coolant corrosive, which corrodes the corrodible coolant barrier, thereby allowing coolant into said hollow body to be seen through said transparency in said first end. In another embodiment, a sensor may be mounted in the hollow body area and electrically to an ECU, which may further be connected to a light. When the coolant barrier corrodes, the sensor is immersed in the coolant, and transmits an electrical signal to the ECU, that sends a signal to a display on the dashboard, and may further initiate other logic and functions, thereby alerting the observer that the coolant corrosiveness should be checked.

The present apparatus is especially adapted for use in engine coolant systems, where unseen coolant corrosion of the engine coolant system due to maintenance lapses or unexpected breakdown in the coolant is a problem.

DETAILED DESCRIPTION OF A PREFERRED EMBODIMENT

Figure 1:
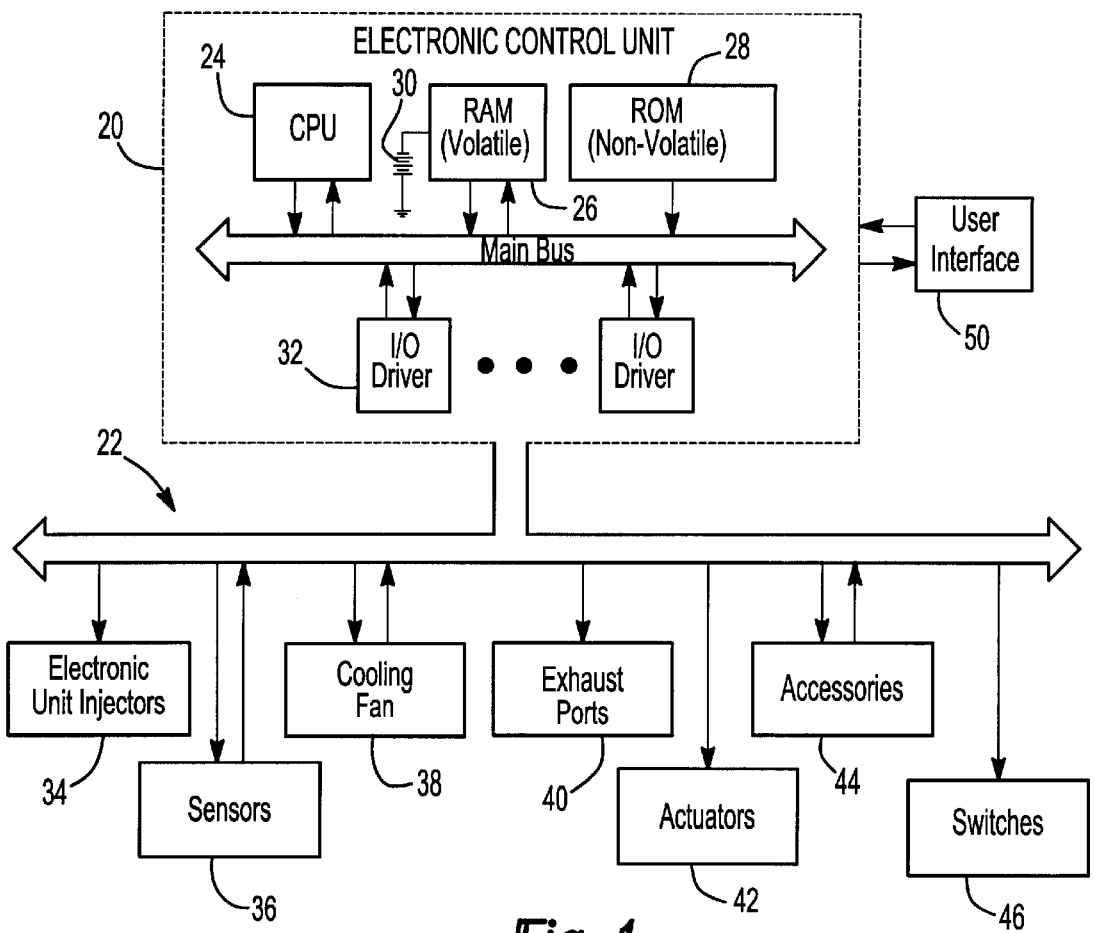
FIG. 1 is a schematic of an electronic control unit in an internal combustion engine.

Turning now to the drawings, wherein like numerals depict like structures, and particularly to FIG. 1, there is shown therein an electronic control unit (ECU) 20 in communication with typical engine compenentry, shown generally by reference numeral 22, and a user interface 50. As shown, the ECU includes a microprocessor 24 having volatile random access memory (RAM) 26, nonvolatile read only memory (ROM) 28, and a battery 30 to maintain at least a portion of the contents of RAM 26 when the main power supply is off or disconnected. Of course, the ECU 20 may contain other types of memory instead of, or in addition to RAM 26 and ROM 28, such as FRAM, EPROM and EEPROM memories, as is well known in the art. The ROM 28 or other nonvolatile memory may contain instructions, which are executed to perform various control and information functions, as well as data tables, which contain calibration values and parameters that characterize normal engine operation. Microprocessor 24 imparts control signals and receives signals from, input and output (I/O) drivers 32. The I/O drivers 32 are in communication with the engine componentry 22 and serve to protect the controller from hostile electrical impulses, while providing the signals and power necessary for engine control according to the present invention. The ECU componentry detailed above is interconnected by data, address and control buses. It should be noted that there are a variety of other possible control schemes that include various combinations of microprocessors and electric or electronic circuits that could perform the same function. The componentry may further include a number of sensors, including a sensor for coolant conditions, such as temperature or corrosiveness, as will be discussed below.

With continuing reference to FIG. 1, preferably, engine componentry 22 includes: a plurality of electronic unit injectors (EUI) 34, each corresponding to a single engine cylinder; a plurality of sensors 36 for indicating engine operating conditions, such as coolant temperature, oil temperature, innercooler temperature, throttle position, turbocharger compressor boost, oil pressure, transmission gear state, cylinder position, or cylinder sequencing; and may also be equipped with a cooling fan 38; and exhaust ports 40. Engine componentry 22 also includes actuators 42 which may include indicator lights, motors, or generators; accessories 44 which may include air-conditioning and vehicle lights; and switches 46 for operating the accessories 44 or for selecting various engine modes, such as power mode, cruise mode or economy mode. It should be appreciated that the ECU may be in communication with other vehicle componentry and microprocessors which control associated vehicle systems, such as the brakes and the transmission.

The user interface 50 is used to store user calibration parameters and retrieve engine historical information logged as a result of diagnostic or malfunction codes. User-calibration parameters may include adjustable limits such as desired engine oil life, maximum road speed or maximum engine speed. Engine historical information may include diagnostic information that is used to assist service personnel performing routine maintenance, or troubleshooting malfunctions, as well as engine and vehicle operator performance in addition to vehicle performance.

Figure 2:
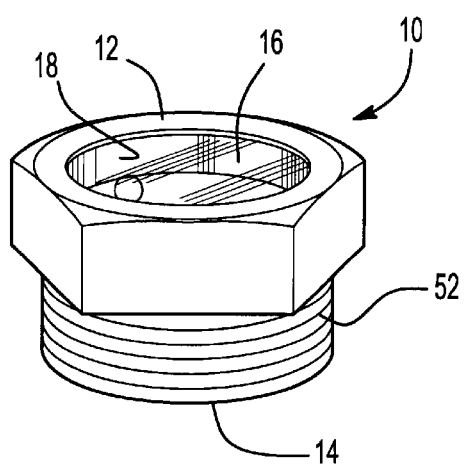
FIG. 2 is a three-dimensional perspective of the apparatus for visually detecting coolant corrosiveness.

FIG. 2 depicts a three-dimensional perspective of one embodiment of the apparatus to detect coolant corrosiveness.

Specifically, in one embodiment, apparatus 10 has opposing ends 12 and 14 in spaced apart relationship to each other, and separated by a sidewall 16 extending substantially unbroken there-between to define a hollow body 18. Body 18 is depicted as tubular, but may be of any configuration. Sidewall 16 may be equipped with threads 52 which may be threadable received in a threaded aperture in an engine coolant system 70, as will be discussed in relation to FIG. 5.

Figure 3:
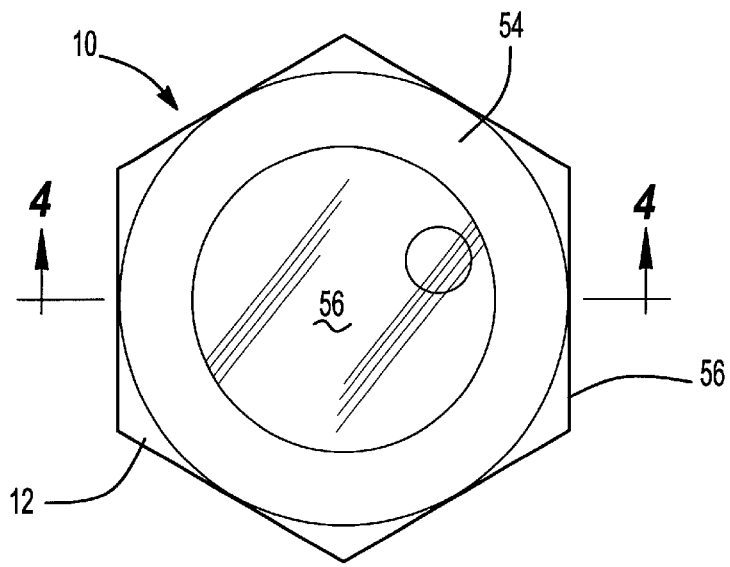
FIG. 3 is a front view of the apparatus for visually detecting coolant corrosiveness.
Figure 5:
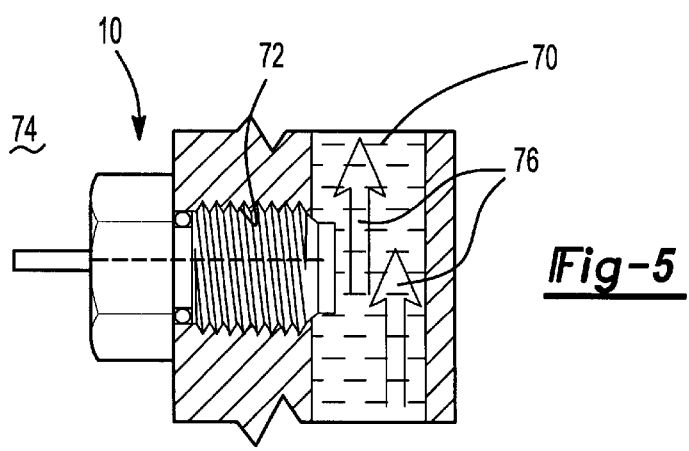
FIG. 5 is a schematic of an engine coolant system showing the apparatus for visually detecting coolant corrosiveness in the engine coolant flow path.
Figure 6:
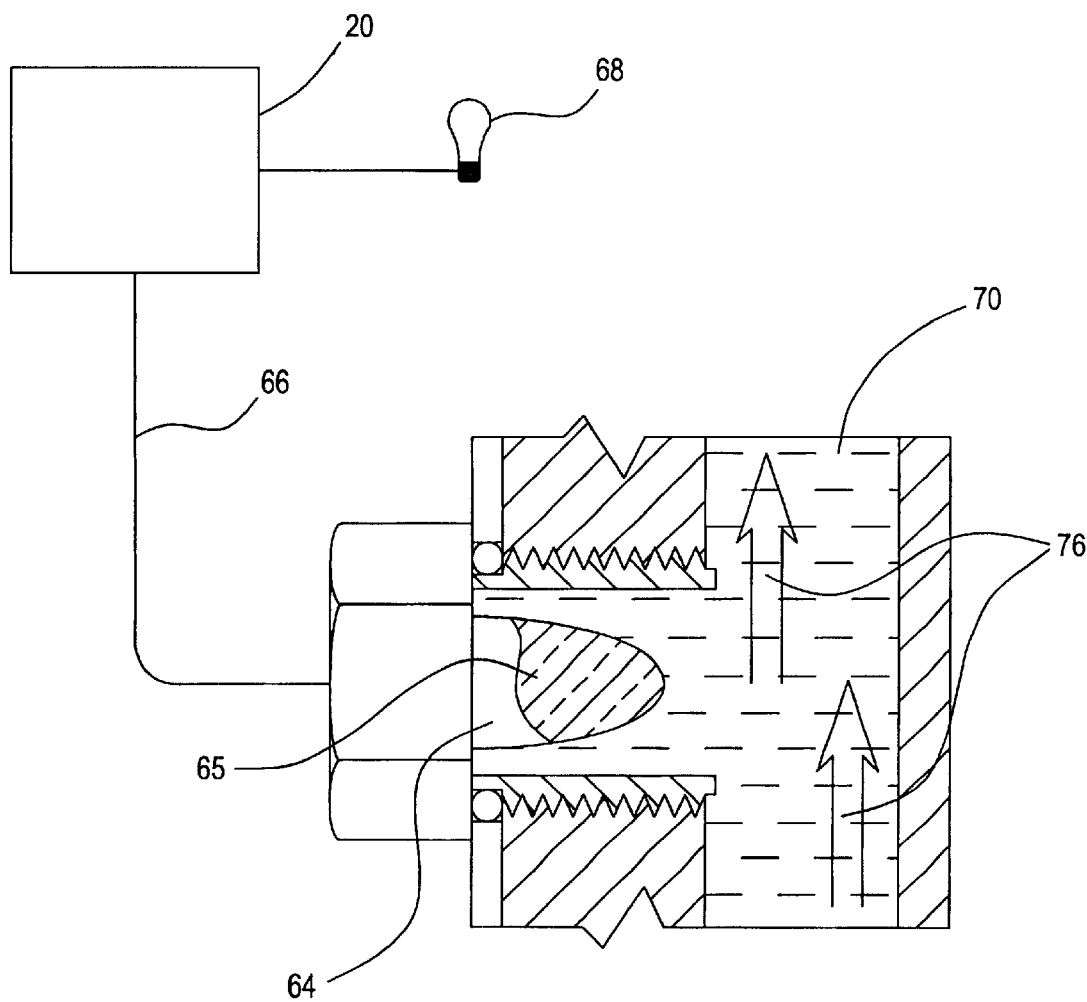
FIG. 6 is another embodiment of the apparatus, showing a sensor coated with a corrodible galvanic material and immersible into the coolant flow path of the vehicle coolant system.

Turning now to FIG. 3, there is shown therein a front view of the apparatus to visually detect coolant corrosiveness. Non-corrosive coolant barrier 54 is affixed to first end 12 and complete occludes the first end, such that a watertight barrier is formed. Non-corrosive coolant barrier 54 has a transparency 56 that comprises at least a portion of the non-corrosive coolant barrier 54. The transparency may be made of plastic, glass or mineral crystal, the only requirement being that it be transparent and able to withstand the environment of an engine coolant system. Note also that the non corrosive coolant barrier 54 may be equipped with facets 56 as a hex nut, to facilitate insertion and removal in an engine coolant system flow path 76, as seen in FIG. 5.

Figure 4:
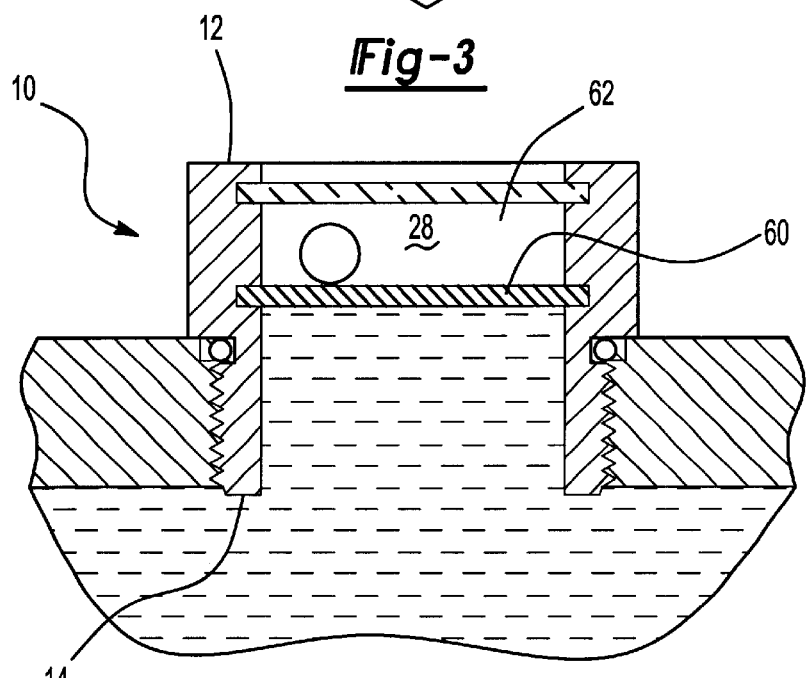
FIG. 4 is a cutaway side view of the apparatus for visually detecting coolant corrosiveness taken along line 3—3 of FIG. 2.

FIG. 4 is a cutaway side view of the apparatus of FIG. 3, taken along line 3—3. Specifically, the corrodible coolant barrier 60 is affixed to the second end such that a watertight barrier is formed at the second end. Note that between the first and second end is an airtight space 28, and this space defines the interior of the hollow body 62. When the coolant is in the prescribed pH range, no coolant enters the interior of the apparatus and when the pH of the coolant is corrosive, the corrodible barrier is corroded, and coolant flows into the interior of the hollow body and is visible through the transparency, thereby alerting a user that the coolant needs maintenance.

In another embodiment, a coolant sensor 64 may be mounted within the airtight hollow body 62 and equipped with electrical connection 66 to the ECU, in a manner described with reference to FIG. 1, which sends a signal to a light 68 mounted in some area visually accessible to an observer, such as a vehicle dashboard. In addition the ECU may store a diagnostic record of the event for future retrieval, or perform other functions of engine control. When the corrodible coolant barrier corrodes, and coolant enters the airtight space and contacts the sensor, a signal is generated that causes the light to illuminate, thereby alerting the observer that coolant corrosiveness should be checked before damage occurs to the coolant system or the engine.

It will be understood that the corrodible barrier is structured to corrode preferentially, rather than other parts of the engine coolant system contacted by the flowing coolant, including parts of the main coolant systems and parts of the engine, such as cylinder sleeves. In this regard, the corrodible barrier may be structured by reference to its physical dimensions, for example its thickness, which typically may be about 0.05 inches, as well as their compositions and physical character so as to preferentially corrode relative to other parts of the engine coolant system contacted by the coolant, such as the heat exchanger or cylinder sleeves, thereby providing a quick visible sign that the coolant system is in need of maintenance.

Corrodible barrier 60 may be comprised of any material wherein a galvanic circuit may be achieved. In particular, the corrodible barrier may be comprised of at least one metal selected from the group consisting of the galvanic series of metals. The preferred galvanic metal is magnesium, or a magnesium alloy. When a magnesium alloy is used, it contains, by weight percent, about 23% Al, one or more of 0.1–0.2% Fe, 2% Pb, 2% Sn, 0.1% Ni, 0.1% Cu, and the balance Mg.

Turning now to FIG. 5, there is a schematic of the engine coolant system 70 of a diesel truck, or any other vehicle, showing the flow path 76 of the coolant. Apparatus 10 is threadably engaged into a threaded aperture 72 in the engine coolant system 70 such that it is in a prominent, easy to see location 74. The apparatus is oriented in the coolant system such that the corrodible barrier is immersed into the coolant system flow path 76, and the transparency, if it so equipped, is exposed for view by an operator. In the event the apparatus is equipped with a sensor, the sensor is arranged to be immersed into the coolant when the corrodible barrier is corroded.

Engine coolants are continuously circulated during operation of the vehicle to remove heat and prevent corrosion of the engine and cooling system. A typical engine coolant is based upon an antifreeze mixture of ethylene glycol, diethylene glycol and water. Recently, organic acids are used with increasing frequency in the place of phosphates, for environmental purposes. Special care needs to be taken not to add additives to engine coolants that react with the organic acids to change the pH of the coolant. So, maintenance of the cooling system and the coolant is even more important, especially with heavy-duty diesel engines.

With the passage of time in service the engine coolant becomes increasingly corrosive. The increase in corrosiveness may be caused by several factors, including, but not limited to, over dilution of the coolant, degradation of one or more of the corrosions inhibitors by heat or aeration, and introduction to the coolant of corrosive species, such as chloride and sulphate ions, in make-up diluent, for example, tap water. The corrodible barrier is structured such that it will rapidly disintegrate by corrosive attack of the engine coolant having a predetermined level of corrosiveness before other parts of the engine system, such as, for example, cylinder sleeves, or other parts of the engine coolant system corrode. Once the corrodible barrier corrodes, the engine coolant fills the hollow body of the apparatus, and is visible in the transparency, or contacts a sensor, which sends a signal to the vehicle ECU, which logs the condition and activates a light, thereby alerting the operator that the coolant system needs maintenance.

In another embodiment of the invention, a sensor may be covered in the coolant corrosive membrane and immersed into the coolant. When the coolant becomes corrosive and dissolves the membrane. The presence of moisture or liquid in the sealed area will therefore be detected by the sensor and the electronics will alert the operator or service personnel that the coolant should be checked or serviced. Once the membrane shielding the sensor has deteriorated, thereby generating the alert, it will need to be replaced after the coolant additive deficiency has been addressed to reset the alert and again have a functioning coolant quality sensor. The coolant sensor may be selected from an optical coolant sensor, a flotation type coolant switch and a conductive coolant sensor.

In any embodiment using a sensor electrically connected to an ECU, the presence of moisture or liquid on the sensor will cause an alert to be sent to the operator or maintenance personnel. The alert could take many forms, such as to store a diagnostic record when the membrane failure occurs including such information as the first occurrence of the diagnostic code in engine hours; the last occurrence of the diagnostic code in engine hours; the date and time of first occurrence; the date and time of last occurrence; the total number of occurrences; and the total engine seconds that the diagnostic code was active. In addition the ECU could broadcast the fault over data links such as the J1587 and/or J1939 links to driver message centers and or maintenance display devices; handheld and PC based diagnostic equipment; and satellite, cellular, radio frequency (RF), or infrared (IR) links to the truck's maintenance facility. Finally, the alert could be a light to check the engine or stop the engine, and these may flash at startup and/or stay lit when the engine is running.

In addition, the ECU may be programmed to promote service of the engine coolant by reducing allowable road speed when the coolant fluid is sensed; reduce allowable horse power when the coolant fluid is sensed; reduce the allowable RPM of the engine when the coolant is sensed or shut the engine down to prevent damage after a preprogrammed elapse of time of operation has occurred after the coolant has been sensed.

While these and other embodiments have been described with particularity, it will be understood by those of ordinary skill in the art that many variations and modification of the described invention will occur without departing from the scope and spirit of the invention as set forth in the appended claims.

We claim:

1. A device to detect the corrosiveness of coolant in an engine coolant system having a flow path for a coolant system, said engine further including an electronic control unit, comprising:

a) a hollow tubular body having first and second opposing ends in spaced apart relation to each other, and a sidewall extending substantially unbroken therebetween; said body being threaded and adapted to be threadably inserted into the flow path of said engine coolant system;

b) a non-corrodible coolant barrier at said first end occluding said first end and forming a watertight seal over said first end;

c) a corrodible coolant barrier at said second end occluding said second end and forming a water tight seal over said second end; said coolant corrodible barrier immersed in said flow path of said engine coolant system and comprised of at least one metal selected from the group consisting of the galvanic series of metals;

d) a sensor mounted in said hollow body between said corrodible and non-corrodible barriers; said sensor electrically connected to said electronic control unit;

whereby changes in coolant pH render the engine coolant corrosive, which corrodes the coolant corrodible barrier before corroding other parts of the engine coolant system, thereby allowing coolant into said hollow body to be contacted by the sensor and thereby cause an alert to be transmitted from the sensor via the electronic control unit to an observer of the corrosiveness of the coolant; and further characterized in said alert includes a first occurrence of the diagnostic code in engine hours; a last occurrence of diagnostic code in engine hours; a date and time of first and last occurrence of membrane failure; a total number of membrane failure occurrences; a total of engine seconds that the diagnostic code is active; a broadcast over a data link to driver message centers, maintenance display devices, hand-held and PC based diagnostic equipment; and a light to signal the membrane failure and signal engine stop.

2. The device of claim 1, wherein said alert signal is broadcast via satellite, cellular, Radio Frequency (RF) or Infrared Links (IR) to a maintenance facility.

3. A device to detect the corrosiveness of coolant in an engine coolant system having a flow path for a coolant system, said engine further including an electronic control unit, comprising:

a) a hollow tubular body having first and second opposing ends in spaced apart relation to each other, and a sidewall extending substantially unbroken therebetween; said body being threaded and adapted to be threadably inserted into the flow path of said engine coolant system;

b) a non-corrodible coolant barrier at said first end occluding said first end and forming a watertight seal over said first end;

c) a corrodible coolant barrier at said second end occluding said second end and forming a water tight seal over said second end; said coolant corrodible barrier immersed in said flow path of said engine coolant system and comprised of at least one metal selected from the group consisting of the galvanic series of metals;

d) a sensor mounted in said hollow body between said corrodible and non-corrodible barriers; said sensor electrically connected to said electronic control unit;

whereby changes in coolant pH render the engine coolant corrosive, which corrodes the coolant corrodible barrier before corroding other parts of the engine coolant system, thereby allowing coolant into said hollow body to be contacted by the sensor and thereby cause an alert to be transmitted from the sensor via the electronic control unit to an observer of the corrosiveness of the coolant; and further characterized in that when said alert is received by the electronic control unit, the electronic control unit institutes a reduction in allowable road speed; a reduction of allowable horse power; a reduction in allowable engine RPM; and an engine shut down to prevent damage after a predetermined period of time has elapsed from the sensing of fluid.

* * * * *